US005728087A

United States Patent [19]

Niedospial, Jr.

[11] Patent Number: 5,728,087

[45] Date of Patent: Mar. 17, 1998

[54] UNIVERSAL FLEXIBLE PLASTIC CONTAINER WITH MULTIPLE ACCESS PORTS OF INVERTED Y SHAPE CONFIGURATION

[75] Inventor: John J. Niedospial, Jr., Burlington, N.J.

[73] Assignee: Bracco Diagnostics, Inc., Princeton, N.J.

[21] Appl. No.: 688,655

[22] Filed: Jul. 30, 1996

[51] Int. Cl.$^6$ .................... A61M 5/00

[52] U.S. Cl. .................... 604/408; 604/403; 604/411; 604/262

[58] Field of Search .................... 604/262, 264, 604/403, 408, 409, 411, 412, 413, 414, 415, 416; 202/181.1, 185.1, 107, 108

[56] References Cited

U.S. PATENT DOCUMENTS

Re. 32,065 1/1986 Ralston et al. .
4,088,166 5/1978 Miller .
4,892,537 1/1990 Carmen et al. .
4,976,707 12/1990 Bodicky et al. .
5,088,994 2/1992 Porat .
5,423,794 6/1995 Adolf et al. .

*Primary Examiner*—John G. Weiss
*Assistant Examiner*—David J. Cho
*Attorney, Agent, or Firm*—Imre Balogh

[57] ABSTRACT

Universal, flexible container with multiple access ports having first and second polymeric sheets, portions of which are embossed, superimposed on each other and sealed together at their periphery defining an interior reservoir with a bottom having a first and second angle of from 5° to 45° each from the center of the bottom and relative to a horizontal plane crossing the center of the bottom portion; and a combination access member of inverted Y shape configuration having:

an IV access port with IV line and control means;
a needle access port; and
a spike access port.

35 Claims, 10 Drawing Sheets

UNIVERSAL FLEXIBLE PLASTIC CONTAINER WITH MULTIPLE ACCESS PORTS OF INVERTED Y SHAPE CONFIGURATION

BACKGROUND OF THE INVENTION

1. Field of the Invention

This invention relates to flexible plastic containers, such as bags and bottles, for the containment and delivery of fluids including diagnostic contrast media, nutrients and drug formulations. More particularly, the invention relates to flexible plastic containers with multiple access ports of inverted Y shape configuration to provide multifunctional utility for the delivery of parenteral solutions by needle, spike and needless luer access and by gross dispensing.

2. Reported Developments

Prior to the discovery and development of polymeric materials, parenteral liquids have been supplied to hospitals exclusively in glass bottles. The disadvantages of glass bottles, such as cost, shipping, storage and disposal, prompted the prior art to provide flexible, sterilizable containers in the forms of bags and bottles for the containment and delivery of parenteral solutions, such as diagnostic contrast media, nutritional and drug formulations. Such containers typically comprise: a flexible plastic sheet formed into a pouch, bag or bottle shape filled with a solution inside therein in a sterile environment; and one or more ports to fill and/or access the solution. Flexible tubing is also provided one end of which is connectable to a port on the container, and the other end connectable to a syringe or catheter pre-inserted into the site of delivery on the patient. Control means are also usually included with the tubing, such as valves and clamps for initiating, controlling and terminating the flow of the liquid to the delivery site. The container, tubing and control means are sterile packaged ready for use.

The prior art containers for medical applications are equipped with a single access port designed to deliver the medical fluids therefrom through an intravenous (IV) line, a spike or needle. Accordingly, the containers are dedicated to one of these modes of delivery, thereby restricting medical personnel to adapt to a single mode of delivery built into the container rather than adapting the container to the mode of delivery best suited to particular circumstances in patient treatment. It would be desirable, especially in an emergency situation, to have available pre-filled medical containers the contents of which could be accessed by any mode of delivery.

Another requirement to be satisfied in flexible containers for delivering parenteral solutions to patients is that by their construction and design they deliver their total contents in a uniform, steady manner and without retaining liquid drops on their walls. By meeting such requirement the medical practitioner can determine the amount of parenteral solution delivered from the container to the patient. The prior art has addressed this requirement, as shown for example in U.S. Pat. No. 4,892,537, which discloses a bag having substantially parallel major sides or edges and converging minor sides which meet at a point forming an obtuse angle of at least 110°. The converging edges are designed to guide the filled bag contents in a substantially unobstructed manner in a funnel-like fashion to an exit port.

U.S. Pat. No. 4,088,166 addresses the problem of incomplete and non-uniform collapse of parenteral solution containers. The incomplete collapse is attributed to the stiffness of the thin-walled polypropylene container which tends to resist collapse to such a degree that the moderate suction pressure exerted on the container by weight of the parenteral solution is insufficient to cause its complete collapse. The non-uniform collapse, on the other hand, is attributed to the observed facts that on some occasions, the bags collapse along the long axis of their cross section, while on other occasions they tend to collapse along both the short axis of the cross-section as well as the long axis. As a result, the medical practitioners cannot determine exactly how much parenteral solution has been delivered out from the container. In order to solve the problem of incomplete and non-uniform delivery, the patentee incorporates gusset portions in the body portion of the container adjacent the shoulder portion. The gusset portions include lines of flexing weakness to facilitate the collapse of the container adjacent the shoulder portion as the contents thereof are withdrawn. The gussets said to facilitate both the lateral and longitudinal collapse of the container as it is emptied.

Medical practitioners have also observed fluid "hold up", i.e., when drops of parenteral solutions tend to remain on the internal walls of the flexible container as the solution is being delivered to the site of administration. The moderate suction pressure exerted on the walls of the container is insufficient to overcome the force existing between the drops of liquid and the walls of the container. Often, as the container is being drained, the emptied portion of the parallel walls adhere to each other further trapping drops of the liquid. As a consequence, the prescribed amount of parenteral solution is not delivered to the patient. Such delivery, especially in traumatic circumstances where a precise amount of a drug must be delivered into the patient, can make the difference between life and death of the patient.

The present invention addresses the problems associated with the lack of complete delivery of content, such as incomplete and non-uniform collapse of the container during administration of the parenteral solution, and hold up of drops of the solution on the walls of the container. The present invention provides means by which the parallel walls of the container are spaced apart from each other by having all or at least portions of the walls embossed which, due to low coefficient of friction, allows relative movements of the walls and prevents sticking.

The present invention provides easy and varied access to the parenteral solution contained in the flexible container by having incorporated therein separate access ports for a needle, spike and IV line.

The present invention also provides a unitary container having needleless luer access and IV line integral with the container requiring no assembly prior to use. Such a unitary container is especially suited for use in both hospital and field emergency situations where assembly of prior art devices, having a bag, tubing, extension tubing, needle and catheter are individually packaged in a kit, would require considerable time prior to use.

SUMMARY OF THE INVENTION

The present invention is directed to a flexible, unitary plastic container, such as a bag, pouch or bottle, for the containment and delivery of parenteral solutions, such as diagnostic contrast media, nutrients and drug formulations to a patient in need of such parenteral solutions.

The universal, flexible container of the present invention may be of any configuration, such as square, round, oval, hexagonal or octagonal. Typically, it is of a generally rectangular configuration which will be described hereunder.

In one embodiment, the universal, flexible, plastic container of the present invention comprises:

(a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferable from 10° to 20° from the center of said bottom portion and relative to a horizontal plane crossing the center of said bottom portion to direct and facilitate the flow of content of the solution contained in the pouch towards the center of said bottom portion; all or at least portions of said interior of said pouch being mechanically deformed to prevent adhesion of said first and second plastic sheets; and (b) a combination access member of inverted Y shape configuration having:

b1) a stem with a proximal end and a distal end, said proximal end located at the bottom, center portion of the pouch sealed between the two sheets in the periphery thereof; and b2) a pair of tines having proximal and distal ends, the proximal ends thereof being integral with the stem of the access member;

the combination access member comprising:

(1) an IV access frangible twist-off port at the distal end of the stem; and an IV line having proximal and distal ends which is attached to the IV access twist-off port at its proximal end while, at its distal end, the IV line is being equipped with a one-way luer slip stopcock, vent and removable cap;

(2) a needle access port located in one of the tines of the combination access member; and (3) a spike access port located in the other of the tines of the combination access member;

said needle and spike access ports being equipped with caps.

This embodiment of the present invention provides: needle access and spike access through the respective access ports; it also provides IV access using the one-way luer slip stopcock located at the distal end of the IV line; and when the IV access frangible twist-off port is separated from the stem, it also provides for bulk delivery by allowing pouring the content out of the pouch.

In another embodiment, the universal, flexible, plastic container of the present invention comprises:

(a) first and second flexible plastic sheets having a generally rectangular configuration superimposed and sealed together at their periphery to form a pouch defining an interior, said pouch having a top and a bottom portion; said bottom portion terminates in a first angle and a second angle of from about 5° to about 45°, preferably of from about 10° to about 30°, and most preferable from 10° to 20° from the center of said bottom portion and relative to a horizontal plane crossing the center of said bottom portion to direct and facilitate the flow of content of the solution contained in the pouch towards the center of said bottom portion; all or at least portions of said interior of said pouch being mechanically deformed to prevent adhesion of said first and second plastic sheets; and (b) a combination access member of inverted Y shape configuration having:

b1) a stem with a proximal end and a distal end, said proximal end located at the bottom, center portion of the pouch sealed between the two sheets in the periphery thereof; and b2) a pair of tines having proximal and distal ends, the proximal ends thereof being integral with the stem of the access member;

the combination access member comprising:

(1) a one-way luer slip stopcock attached to the distal end of the stem;

1a) an IV access frangible twist-off port attached to the one-way luer slip stopcock; and 1b) an IV line, having proximal and distal ends, attached to the IV access twist-off port at the proximal end thereof, while at its distal end, the IV line is being equipped with a luer lock and cap; and (2) a needle access port located in one of the tines of the combination access member; and (3) a spike access port located in the other of the tines of the combination access member;

said needle and spike access ports being equipped with caps.

This embodiment of the present invention, in addition to providing access to the content of the pouch using the needle and spike access ports, and IV access through the luer lock and removable cap, also provides for separating the IV line form the luer slip stopcock and allowing the user to attach a different IV line to the one-way luer slip stopcock thereby to allow access and control the flow of the content of the pouch.

In this embodiment of the present invention, the stem of the combination access member is equipped with a vent, located preferably close to the proximal end thereof and spaced from the location of the tines.

Preferably the top portion at the periphery of the pouch comprises at least one hole for suspending the container when it is in use for delivering the content thereof to the delivery site.

Preferably the bottom portion at the periphery of the pouch comprises at least one, and preferably a plurality, of holes to facilitate suspending the container during the filling process.

Additional features and advantages of the present invention will be apparent from the drawings and of the detailed description.

Figure 1:
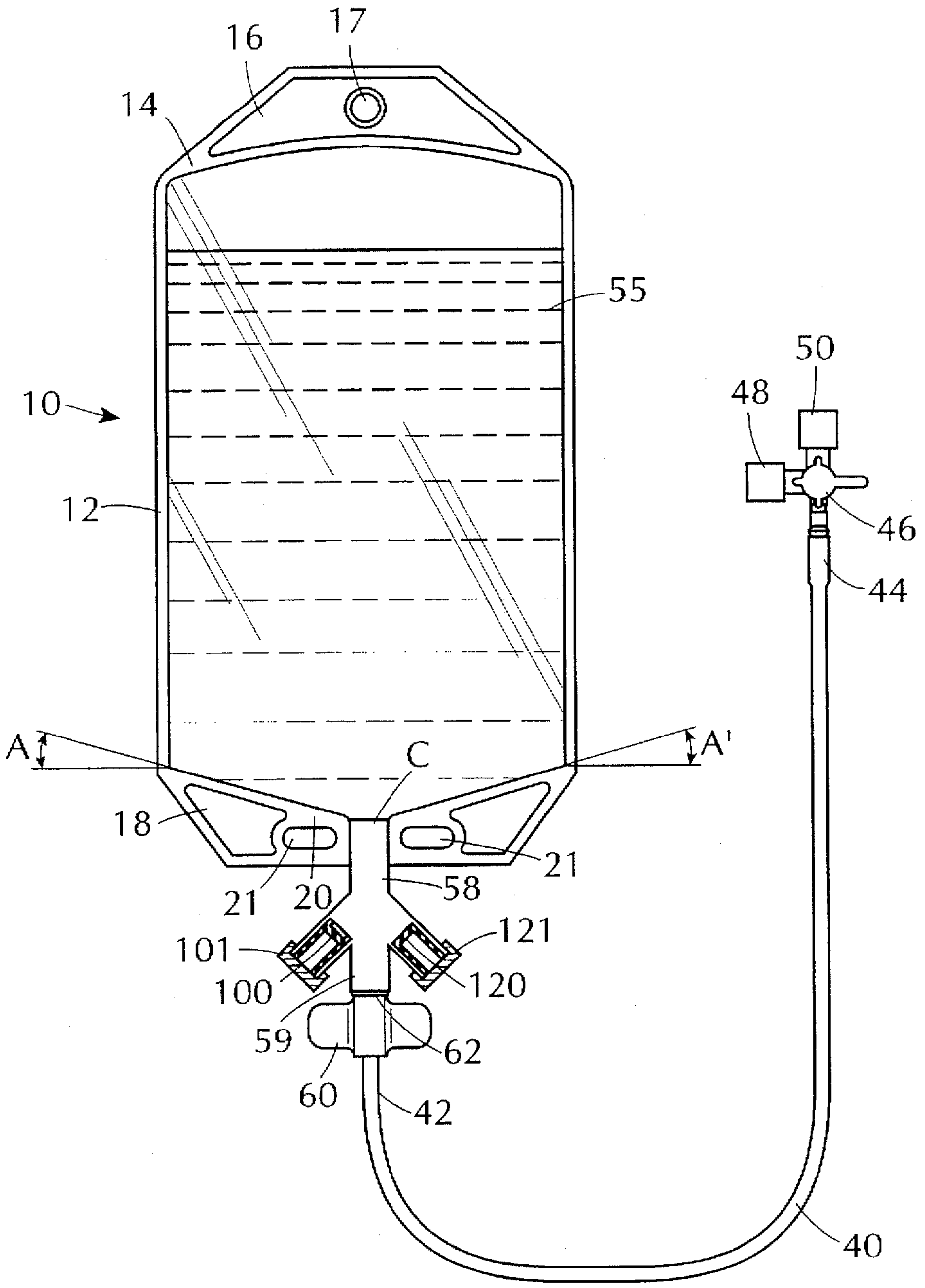
FIG. 1 is a plan view of a universal flexible container in accordance with the present invention showing.
Figure 2:
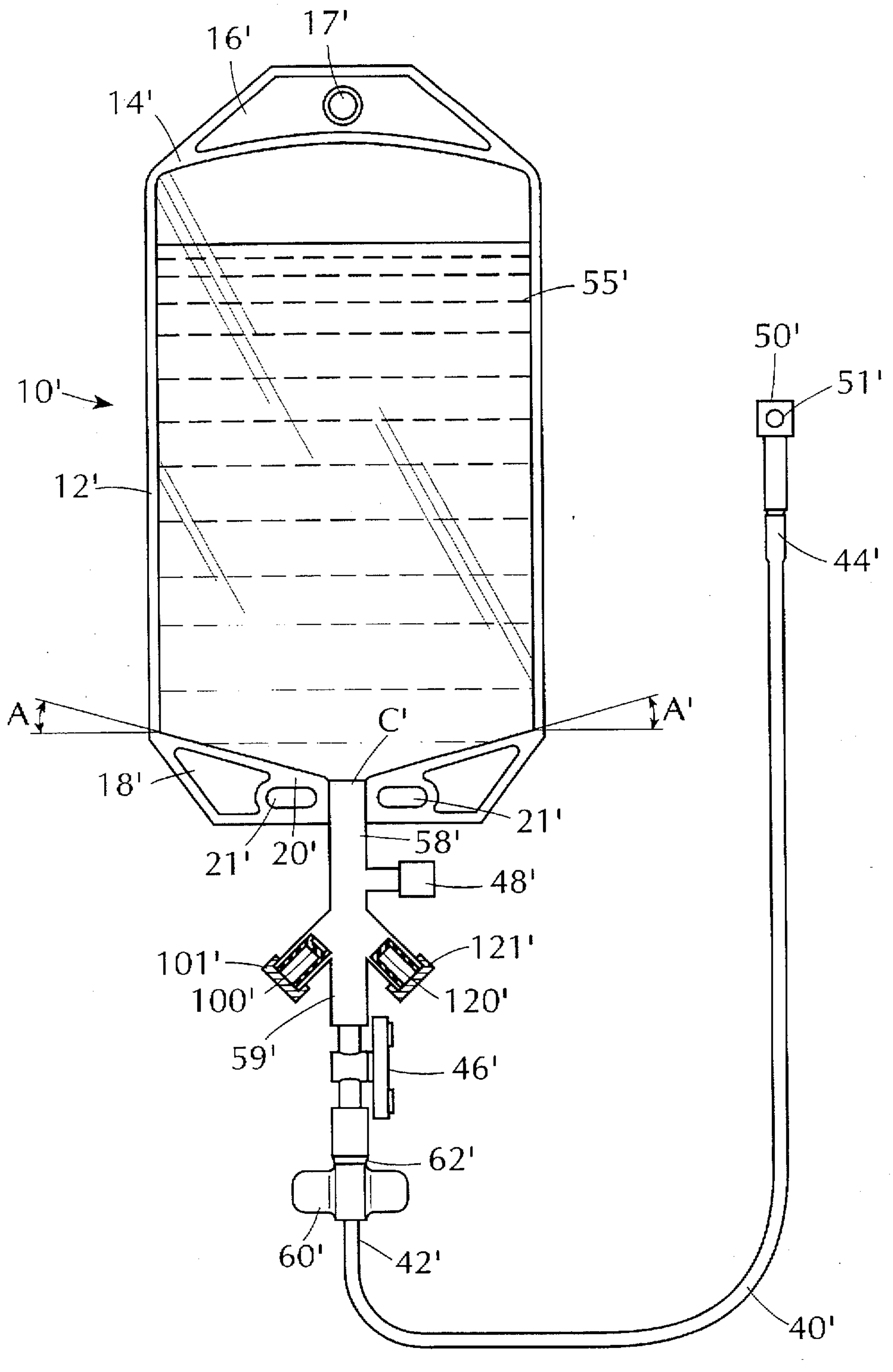
Figure 3A:
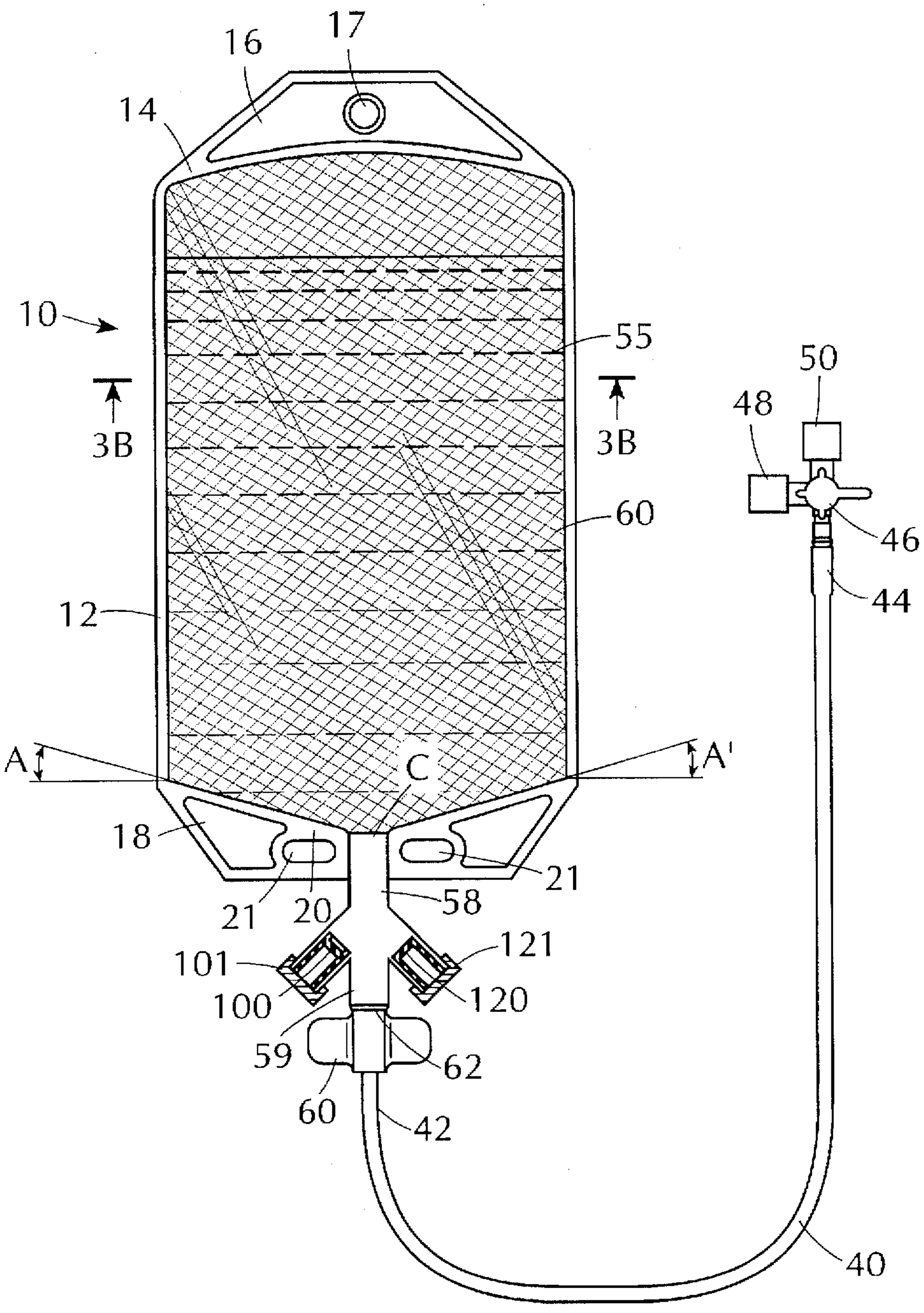
Figure 3B:
Figure 4A:
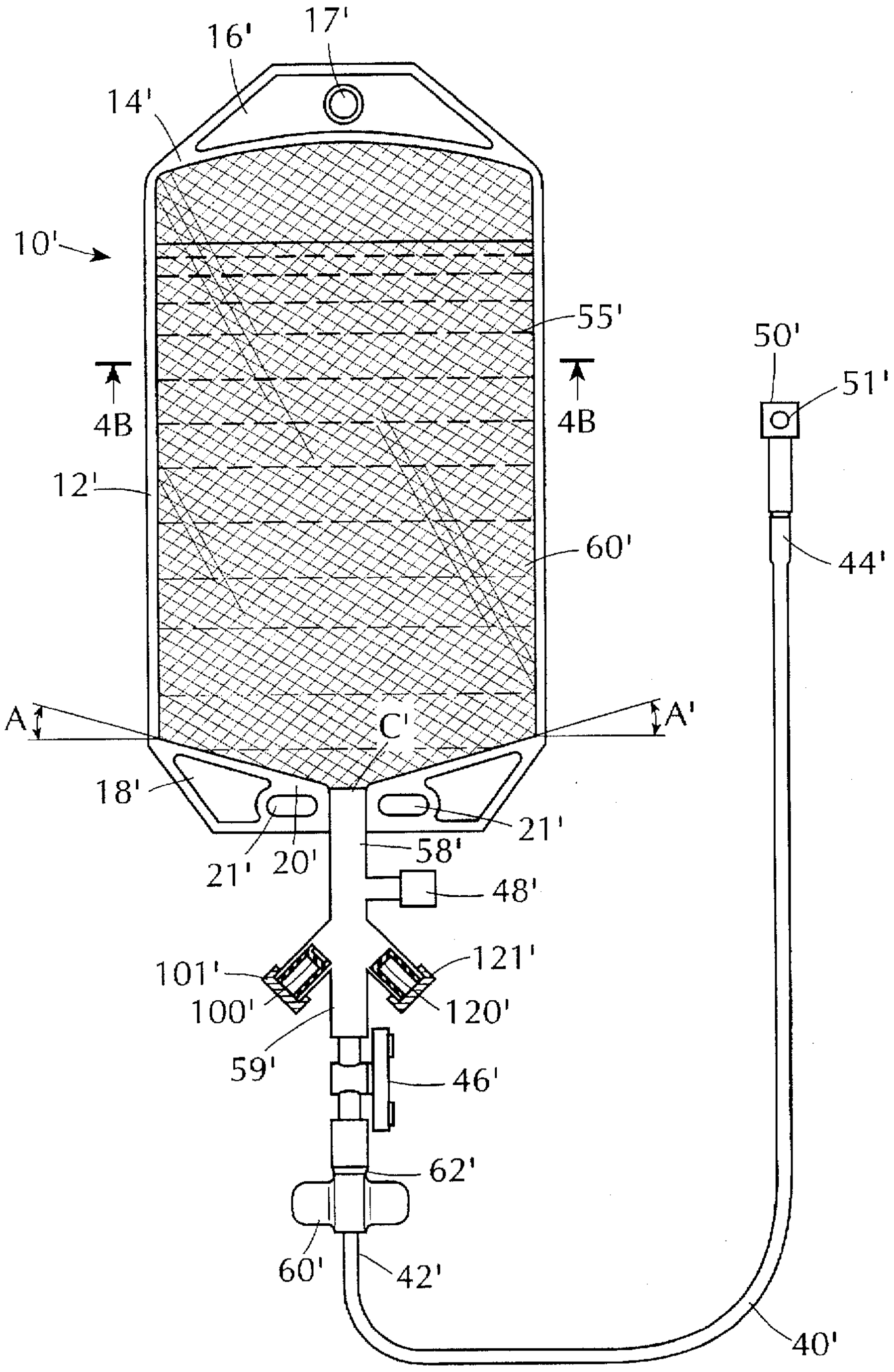
Figure 4B:
Figure 5A:
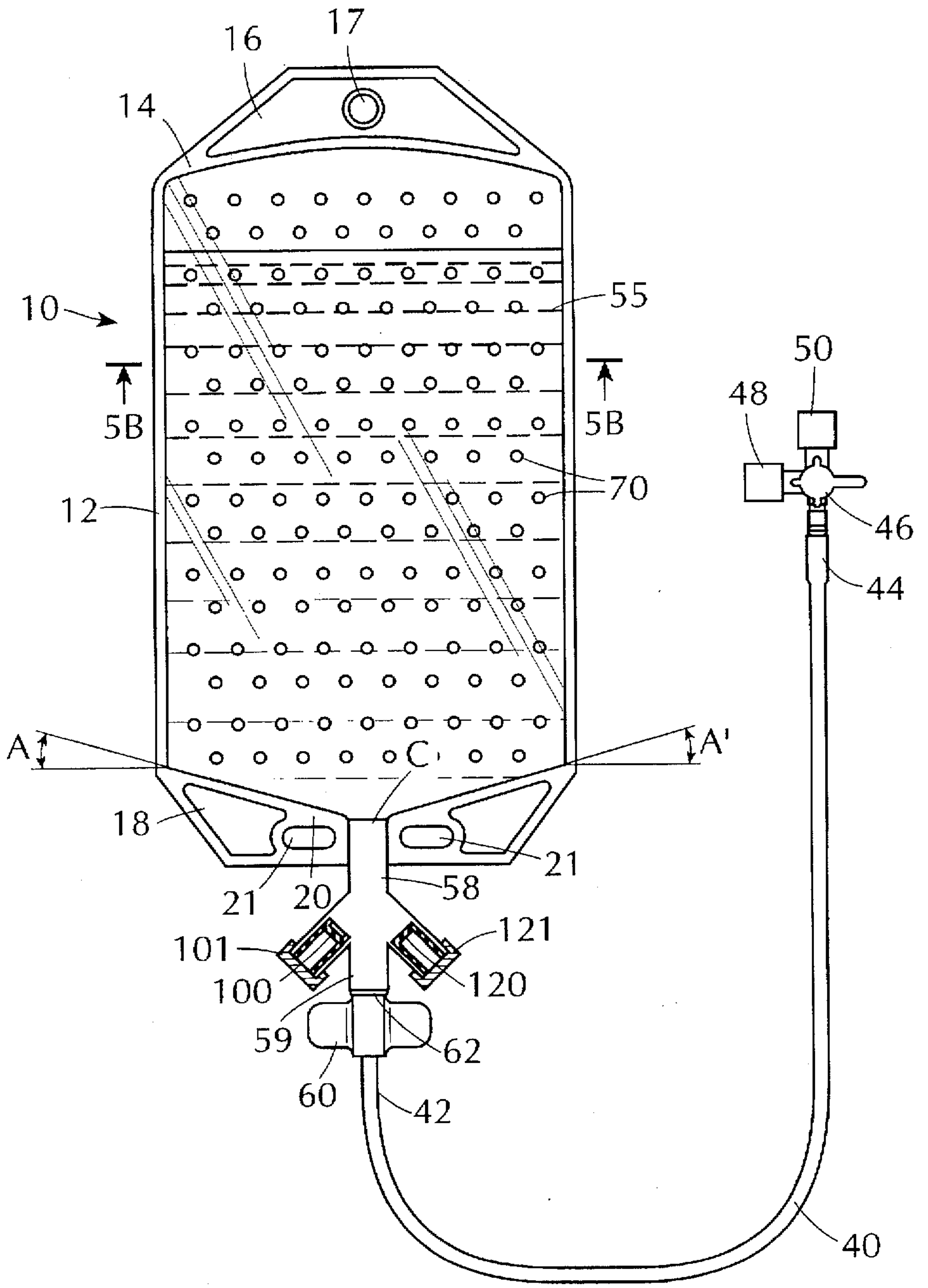
Figure 5B:
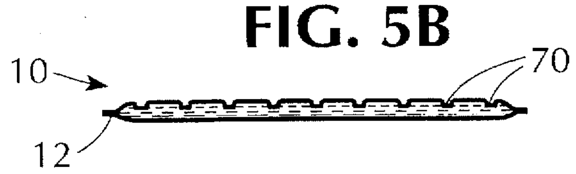
Figure 6A:
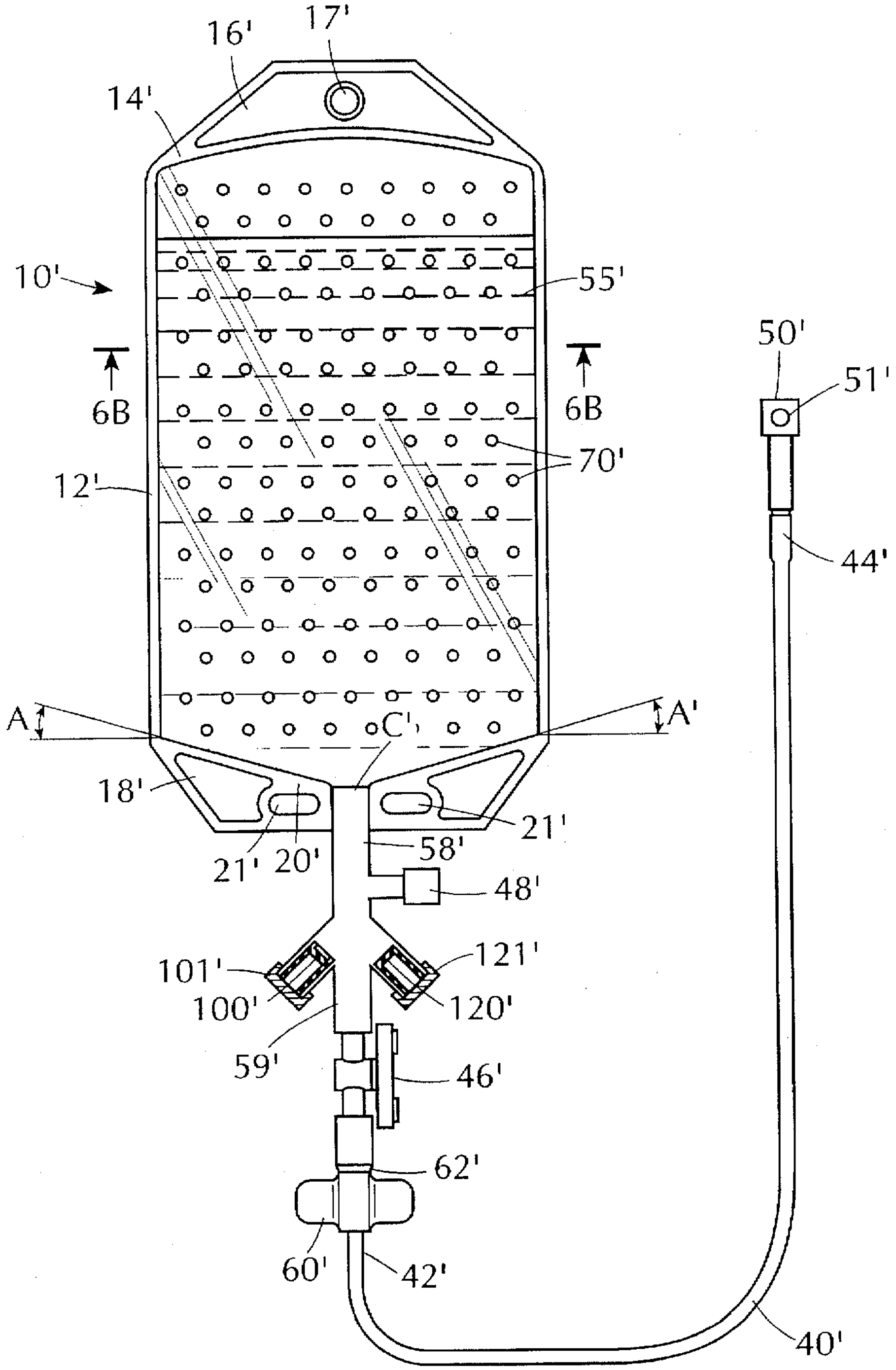
Figure 6B:
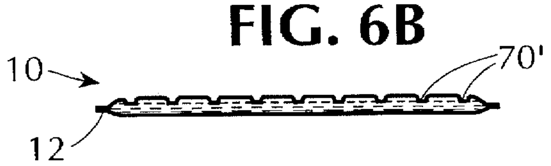
Figure 7A:
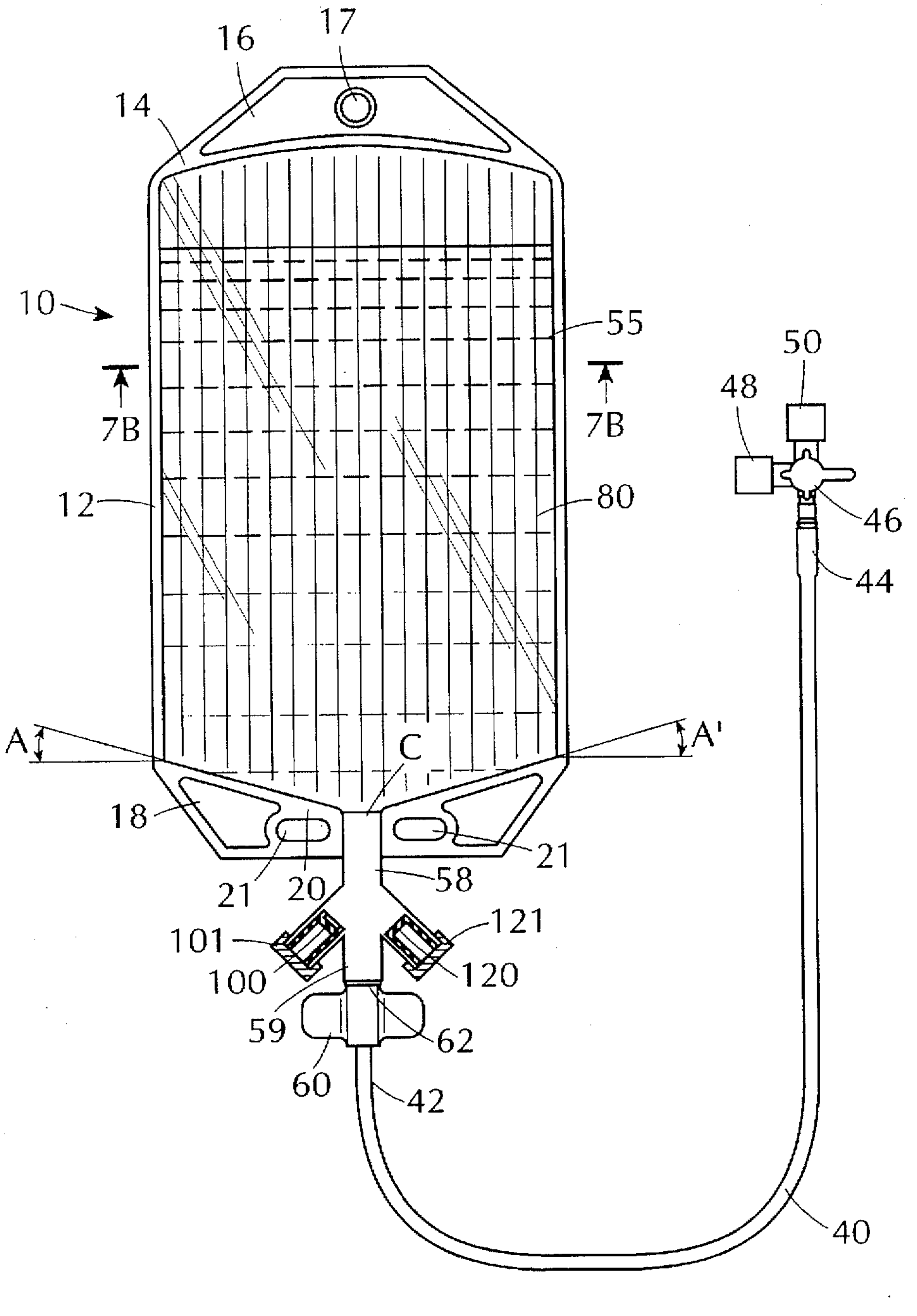
Figure 7B:
Figure 8A:
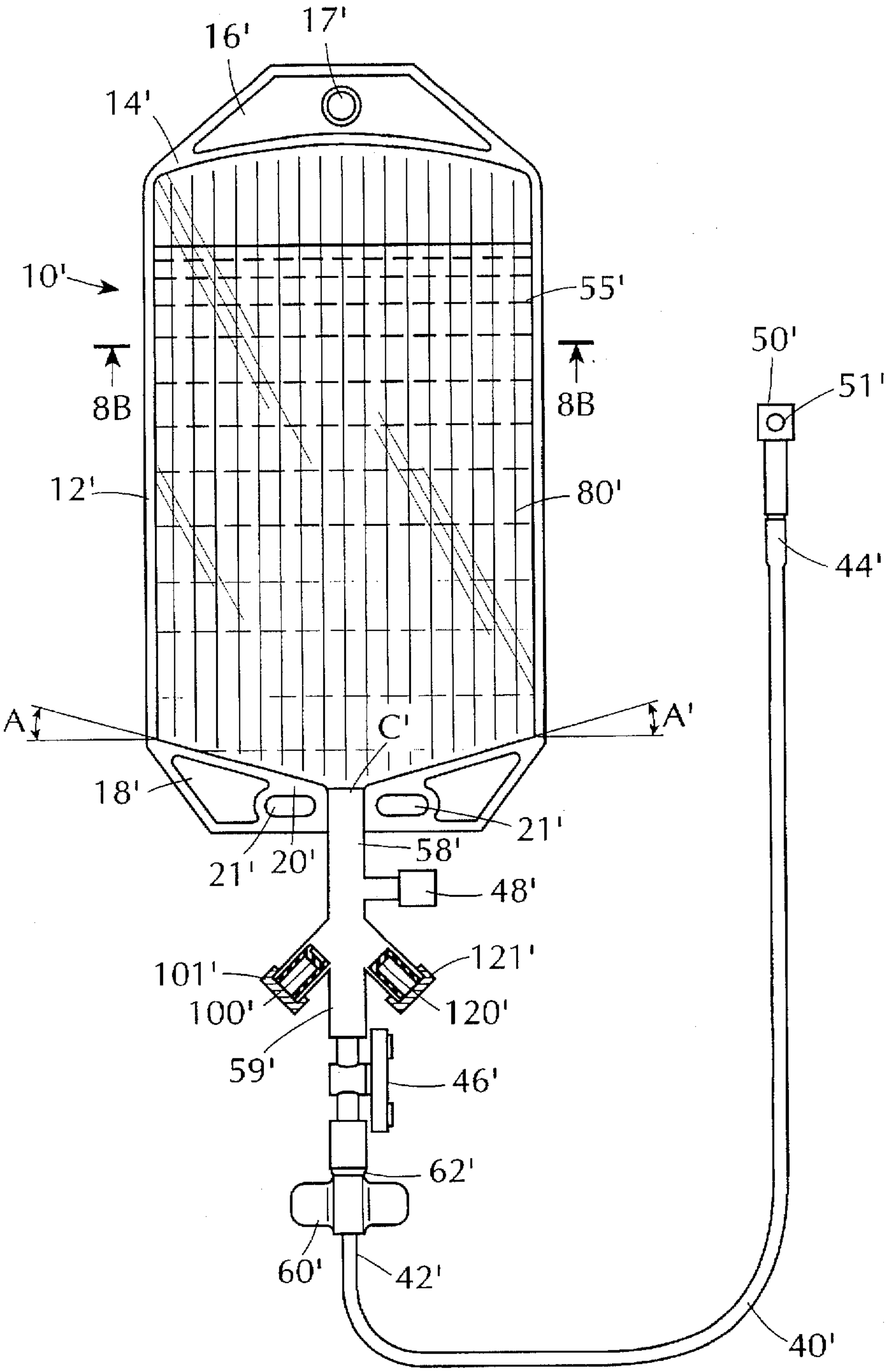
Figure 8B:
Figure 9A:
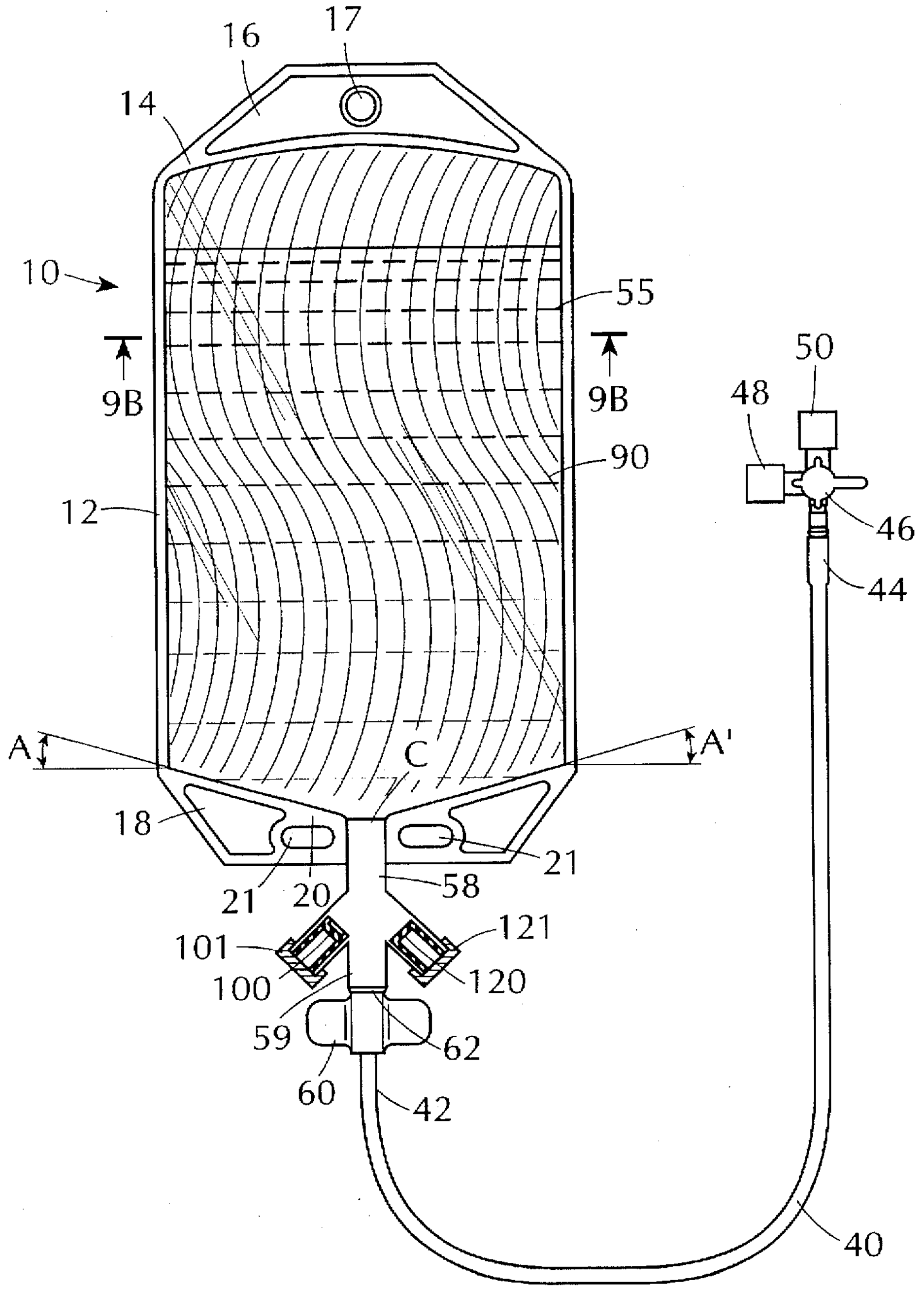
Figure 9B:
Figure 10A:
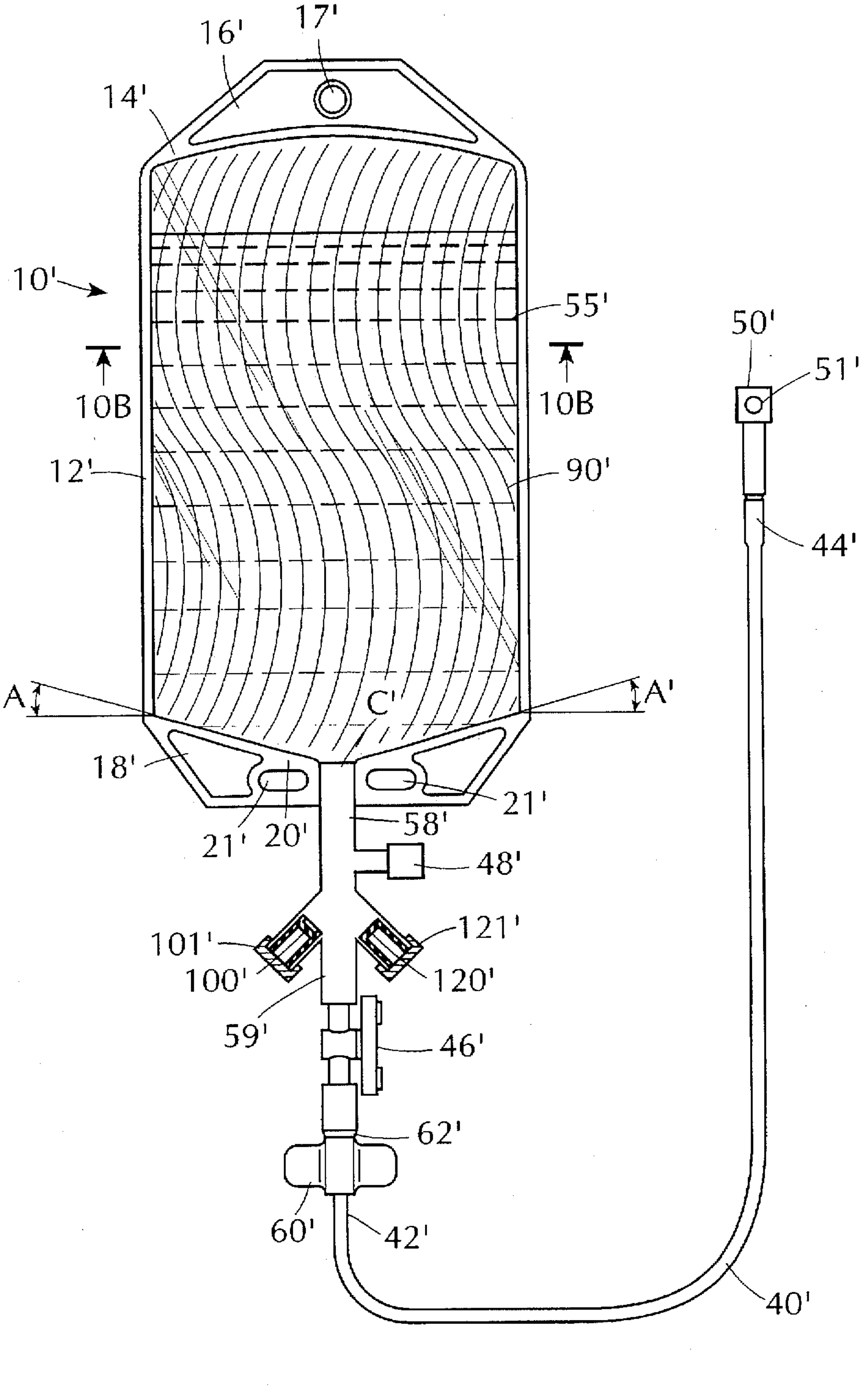
Figure 10B:

a) a pouch; and b) a combination access member of inverted Y shape configuration having a stem with proximal and distal ends and a pair of tines comprising:

1) an IV access frangible twist-off port at the distal end of the stem; and an IV line having proximal and distal ends, said IV line is attached to the IV access twist-off port at its proximal ends, while at its distal end the IV line is equipped with a one-way luer slip stopcock, vent and removable cap;

2) a needle access port located in one of the tines of the combination access member; and 3) a spike access port located in the other of the tines of the combination access member;

FIG. 2 is a plan view of another embodiment of the present invention showing:

a) a pouch; and b) a combination access member of inverted Y shape configuration having a stem with proximal and distal ends and a pair of tines comprising:

1) a one-way luer slip stopcock attached to the distal end of the stem; and an IV line, having proximal and distal ends, attached to the one-way luer slip stopcock by its proximal end, while at its distal end the IV line is equipped with a luer lock and removable cap;

2) a needle access port located in one of the tines of the combination access member; and 3) a spike access member located in the other of the tines of the combination access member;

FIG. 3A is plan view of the universal, flexible container shown in FIG. 1 one wall of which is embossed in a checkerboard fashion;

FIG. 3B is a cross-section of the universal, flexible container shown in FIG. 3A taken along the line 3B—3B;

FIG. 4A is a plan view of the universal, flexible container shown in FIG. 2 one wall of which is embossed in a checkerboard fashion;

FIG. 4B is a cross-section of the universal, flexible container shown in FIG. 4A taken along the line 4B—4B;

FIG. 5 is a plan view of the universal, flexible container shown in FIG. 1 one wall of which is embossed in a dotted fashion;

FIG. 5B is a cross-section of the universal, flexible container shown in FIG. 5A taken along the line 5B—5B;

FIG. 6A is a plan view of the universal, flexible container shown in FIG. 2 one wall of which is embossed in a dotted fashion;

FIG. 6B is a cross-section of the universal, flexible container shown in FIG. 6A taken along the line 6B—6B;

FIG. 7A is a plan view of the universal, flexible container shown in FIG. 1 one wall of which is embossed with vertically oriented channels;

FIG. 7B is a cross-section of the universal, flexible container shown in FIG. 7A taken along the line 7B—7B;

FIG. 8A is a plan view of the universal, flexible container shown in FIG. 2 one wall of which is embossed with vertically oriented channels;

FIG. 8B is a cross-section of the universal, flexible container shown in FIG. 8A taken along the line 8B—8B;

FIG. 9A is a plan view of the flexible container shown in FIG. 1 one wall of which is embossed with vertically oriented S-shape channels;

FIG. 9B is a cross-section of the universal, flexible container shown in FIG. 9A taken along the line 9B—9B;

FIG. 10A is a plan view of the universal, flexible container shown in FIG. 2 one wall of which is embossed with vertically oriented S-shape channels; and FIG. 10B is a cross-section of the universal, flexible container shown in FIG. 10A taken along the line 10B—10B.

DETAILED DESCRIPTION OF THE INVENTION

The present invention provides a universal, flexible plastic container, in the shape of a bag, pouch or bottle, for the containment and delivery of diagnostic contrast media, nutrients and drug formulations. In the drawings where like numerals indicate like elements or portions, the reference character 10 and 10' in FIGS. 1 and 2 indicate the container which, in a preferred embodiment, is a pouch-like device, comprising two superimposed sheets of suitable length and width made of flexible or pliable materials, such as polymeric materials including polyethylene, polypropylene, and preferably thermoplastic materials. The superimposed sheets forming the pouch-like container are preferably made of transparent materials so as to allow observation of the amount of its content during the filling operation and delivery thereof to the patient. Each of the superimposed transparent sheets is preferably formed of multilayers of laminated thin films at least one of which constitutes a barrier which is impervious to atmospheric gases, moisture and bacteria. The superimposed sheets are preferably flat welded to each other so as to form the pouch whose volume is zero before it is filled with a parenteral solution. When the pouch is filled or partially filled as shown by 55 in FIG. 1 and 55' in FIG. 2, it assumes the shape of a small cushion. The superimposed sheets are joined together along marginal areas 12, 12', 14, 14', 16, 16', 18, 18', 20 and 20' as shown in FIGS. 1 and 2 respectively.

Reference to embodiment of one of the present invention will be made by numerals without superscripts, while reference numerals with superscripts will relate to the second embodiment of the present invention.

The bottom portion of pouch 10 or 10' terminates in first angle A and second angle A' from the center C or C' of said bottom portion and relative to a horizontal plane crossing the center C or C' of said bottom portion to direct and facilitate the flow of content contained in the pouch towards a combination access member of inverted Y shape configuration 58 or 58'. Angles A and A' are of from about 5° to about 45°, preferably from 10° to 30° and most preferably from 10° to 20°.

Combination access member, having an inverted Y shape configuration is located at center C or C' of the bottom portion of pouch 10 or 10' comprising:

a steam having a proximal end 58 or 58' and a distal end 59 or 59'; and a pair of tines integral with the stem. The proximal end 58 or 58' is located at the bottom center portion of the pouch and below a horizontal plane crossing the center C or C' of said bottom portion so that all the liquid content of the pouch can be drained from the pouch into the stem. The proximal end 58 or 58' is sealed between the two superimposed sheets in the periphery thereof which form the pouch.

A pair of tines extend from and are integral with the stem forming the inverted Y shape of the combination access member. One of the tines constitute the needle access port 100 or 100' and is covered by cap 101 or 101'. The other of the tines constitute the spike access port 120 or 120' and is covered by cap 121 or 121'. The cap covering the needle and spike access ports maintain sterility of content of the pouch until the point of use.

Referring to FIG. 1, the stem of the combination access member is attached at its distal end 59 to frangible twist-off port 60. The frangible twist-off port is integral with IV line or tube 40 having proximal end 42 and distal end 44. Frangible twist-off port may be separated from the stem of the combination access member at breakaway area 62. Such separation provides for gross removal of the contents if required.

IV line or tubing 40 is equipped at its distal end 44 with a one-way luer slip stopcock 46, a vent 48 and cap 50. The IV line 40 with the frangible twist-off port 60 may be attached to the stem of the combination access member during the manufacturing, prior to filling or after the pouch has bee filled. Alternatively, the combination access member may be sealed between the superimposed sheets that form the pouch at the periphery thereof after the pouch has been filled.

FIG. 2 shows another embodiment of the present invention in which the pouch 10' is the same as the pouch 10 shown in FIG. 1, however, the combination access member is configured as follows.

The stem of the combination access member at its distal end 59' is attached to the luer slip stopcock 46' which, in turn, is attached to frangible twist-off port 60' through breakaway area 62'. Frangible twist-off port 60' is integral with the proximal end 42' of IV line 40. IV line at its distal end 44' is equipped with her lock 51' and cap 50'. Vent 48' is preferably positioned at proximal end 58' of the stem, however, it may be positioned at the distal end 44' of IV line 40 or as an integral part of one-way luer slip stopcock 46'. This embodiment of the present invention provides for delivery of contents of the pouch through the IV line, which line, prior to opening the one-way luer slip stopcock 46', is empty. Further, the frangible twist-off port 60' allows removal of the IV line 40' for those circumstances when a different IV line is used: upon removal of the frangible twist-off port 60' the one-way luer slip stopcock with female luer slip connection can be joined with the male luer member of another IV line.

Referring to FIGS. 1 and 2, access to needle access port 100 or 100' using a steel needle is gained by removing caps 101 or 101'. Access to spike access port 120 or 121 using a plastic spike is gained by removing caps 120 or 121'.

Marginal areas 16 and 16' in FIGS. 1 and 2 preferably comprise at least one hole 17 or 17' for suspending the pouch when it is in use for delivering the content of the pouch to a delivery site.

Marginal areas 20 and 20' in FIGS. 1 and 2 preferably comprise at least one, and more preferably a plurality, of hole(s) 21 and 21' to facilitate suspending the pouch during the filling process.

The universal, flexible container of the present invention may be used for delivering a single dose, multi-dose or a bulk of parenteral solution. The one-way stopcock serves as a means to control flow during sterilization, such as autoclaving, by preventing outward flow, and during drug delivery as required in multidose or bulk pack dispensing. The needle and spike ports, along with the IV access port, allow access to the drug in the pouch by means that happen to be available under any circumstances.

In addition to providing multiple access ports, the present invention provides further improvement in flexible containers designed for delivering parenteral solutions, such as diagnostic contrast media and drug formulations.

It was suprisingly discovered that if the inside wall of the first sheet or the second sheet forming the pouch 10 of FIG. 1 or pouch 10' of FIG. 2 is embossed, fluid hold up in the form of drops adhering to the inside walls can be reduced or eliminated and the walls, as the content of the pouch is being drained into the injection site, adhering together and further trapping drops of the fluid, can be prevented. In accordance with this discovery there are provided the following preferred embodiments of the invention.

Referring to FIG. 3A and FIG. 3B, the inside wall of first sheet of pouch 10 shown in FIG. 1 is embossed in a checkerboard manner 60, the checkerboard consisting of squares the 90° angles of which pointing downward towards the center C of the pouch. The size of the individual squares may be in the range of from 0.01 to 10 $mm^2$ or larger. The size of the individual squares may vary the determination of which would be influenced by the viscosity and the surface tension of the parenteral liquid for the delivery of which the pouch is intended.

While the inside wall of both first sheet and second sheet may be embossed, it was observed that the pouch functions better in terms of eliminating fluid hold up and preventing the superimposed walls from sticking together when only one inside wall of the first or second sheet is embossed.

FIG. 4A and FIG. 4B show the embodiment described in FIG. 2, except that the inside wall of first sheet of pouch 10' is embossed as described in FIGS. 3A and 3B.

Referring to FIG. 5A and FIG. 5B, the inside wall of first sheet of pouch 10 of FIG. 1 is embossed with dots or micro circles 70 in a spaced relationship from each other. The dots or circles may vary in diameter from 5 microns to several mms and may be spaced from each other of from about 10 microns to about 10 mms or longer. While both inside walls of the first sheet and second sheet may be embossed, it is preferred that only the first sheet or second sheet be embossed.

FIG. 6A and FIG. 6B show the embodiment described in FIG. 2, except that the inside wall of first sheet of pouch 10' is embossed 70' as described in FIGS. 5A and 5B.

Referring to FIG. 7 and 7B, the inside wall of first sheet of pouch 10 shown in FIG. 1 is embossed 80 in vertical channel configuration in spaced relationship from each other. The width of the individual channels may be in the range of from about 0.01 to about 10 mm or larger. The channels may be spaced from each other of from about 10 microns to about 10 mms. While both inside walls of the first sheet and second sheet may be embossed, it is preferred that only one inside wall of the first or second sheet be embossed.

FIG. 8A and FIG. 8B show the embodiment described in FIG. 2, except that the inside wall of first sheet of pouch 10' is embossed 80' as described in FIGS. 7A and 7B.

Referring to FIG. 9A and FIG. 9B, the inside wall of first sheet of pouch 10 of FIG. 1 is embossed 90 with vertically oriented channels which have a slight S-shape configuration in a spaced relationship from each other. The size of the width of individual channels may be in the range of from about 0.01 to about 10 mms or larger. The channels may be spaced from each other of from about 10 microns to about 10 mms. While both inside walls of the first sheet and second sheet may be embossed, it is preferred that only one inside wall of the first or second sheet be embossed.

FIG. 10A and FIG. 10B show the embodiment described in FIG. 2, except that the inside wall of first sheet of pouch 10' is embossed 90' as described in FIGS. 9A and 9B.

Materials of Construction

The flexible container of the present invention is made of known polymeric materials having properties which make them suitable for sterile delivery of parenteral liquids. The sheets for forming the walls of the container are preferably multilayer sheets and characterized by heat resistance, gloss, strength, flexibility, and chemical inertness. Preferably the sheets are transparent or at least translucent enabling visual inspection of the contents at all times during delivery of content form the container to the patient. The container must be sterilizable, preferably by heat, along with its content. At least one layer of the sheet must be impervious to atmospheric gases and to steam. Preferably, the internal surface of the pouch in contact with the parenteral solution should be impervious to gases and steam. The interior layer in contact with the parenteral solution must not contain any toxic agents or even plasticizers which could leach out and contaminate the solution. The sheet may be made, for example, from polyvinylidene chloride sandwiched between two polyethylene or polyvinylacetate layers. The polyvinylidene chloride constitutes the impervious barrier. Further layers may be added to the face or back of the sheet, if desired, such as a polyolefin, preferably, polyethylene. Polyvinyl chloride is also suitable for the construction of the sheet and is well-accepted by the prior art for use in containers for medical fluid collection and delivery. Typical properties of polyvinyl chloride films include: a thickness of about 380 micron; a tensile strength of about 240 kg/cm$^2$; a moisture vapor transmission rate of about 14–20 (g/m$^2$/day at 38° C., 100% RH); and an oxygen barrier of 650 (cc/m$^2$/day at 23° C., 0% RH, bar. CRYOVAC® sterlizable medical films (W. R. Grace and Co.) are especially suitable to construct the sheets used in the present invention. The films comprise a polyethylene layer sandwiched between polyester outer layers sealed together by a modified propylene copolymer. Typical properties of the film include: a thickness of about 190 micron; a tensile strength of about 250 kg/cm$^2$; a moisture vapor transmission rate of 5 (g/m$^2$/day at 38° C., 100% RH); and an oxygen barrier of about 1500 (cc/m$^2$/day at 23° C., 0% RH, bar).

Other preferred polymeric films or sheets for constructing the universal, flexible container of the present invention include: copolyester ether monolayer films, such as polycyclohexanedimethylcyclohexane dicarboxylate elastomer made by Eastman Chem. Co.; and ethyl vinyl acetate made by Stedim, Inc. It is important that the fluid contacting layer of the multilayer sheet contain no plasticizer which may contaminate the fluid content of the container. Preferably, no plasticizer should be used at all on any of the multilayers to form the universal, flexible container of the present invention.

The sheets used in the present invention may be embossed with the described configuration by techniques known in the art. Alternatively, the layer constituting the internal liquid contacting layer of the sheet may be embossed prior to forming the multilayer sheets.

Access ports and tubing used in the present invention may be made of polyvinyl chloride which are sold commercially for use in medical devices. Other port and tubing materials may also be used, such as CRYOVAC® Port Tubing (W. R. Grace & Co.) which comprise three concentric layers of polymeric materials: a polyolefin layer is sandwiched between an outer layer of modified propylene copolymer and an inner layer of ethylene vinyl acetate or polyvinyl chloride.

Process of Making and Using the Container

The flexible plastic container in the form of a bag, pouch or bottle is made of two rectangular sheets of polymeric materials one of which is embossed and flat welded together on four sides so as to define between the two sheets and the four welded sides a reservoir. The volume of the container is zero before it is filled and typically has an internal volume capacity of from about 50 to about 5,000 ml when it is filled with a medical fluid, such as a parenteral solution.

Combination access member 58 or 58', needle access port 100 or 100', and spike access port 120 or 120' can be made by blow molding or other techniques known in the art. IV line tubing 40 or 40', one-way luer slip stopcock 46 or 46', cap 50 or 50', vent 48 or 48' are commercially available.

Combination access member 58 or 58' are sealed between the superimposed sheets by the same welding process used to seal the superimposed sheets together. Upon completion of the welding process the container is suspended via holes 21 or 21', followed by filling the container through IV line 40 or 40' with the desired fluid. Alternatively, the container may be sealed by heat welding at its four edges except at its bottom center portion C or C' and filled with the desired fluid prior to sealing combination access member 58 or 58' between the superimposed sheets. With either process, the universal, flexible container of the present invention, when it is filled with the desired fluid, provides for instant delivery via IV, needle, spike or bulk.

In the process of delivering the medical fluid to a patient using the IV access port, the container 10 or 10' is suspended via hole 17 or 17', cap 50 or 50' is removed and a spike or similar means is engaged with end of tubing 40 or 40'. One way luer slip stopcock assembly is turned to open position thereby starting the flow of medical fluid from the container through the tubing and spike to the site of delivery on the patient. Vent 48 or 48' allows outside air to replace the drained medical fluid in the container so that fluid flow is steady and continuous. If discontinuation of fluid flow is desired, the one-way luer stopcock assembly is turned to the stop position. If fluid delivery is desired using the needle or spike access ports, the container is suspended via hole 17 or 17', caps 101 or 101' or 121 or 121' are removed and needle or spike is inserted into the respective ports to enable delivery of the medical fluid to the desired site on the patient.

If bulk delivery is desired, frangible twist-off port 60 or 60' is removed at breakaway area 62 or 62' thereby allowing bulk fluid flow from the container.

If another IV line is desired to be used, the embodiment shown in FIG. 2 provides for such eventuality: stopcock 46' is closed, followed by removing frangible twist-off port 60' at breakway area 62' to expose the luer connection which is part of the stopcock. The desired IV line is then connected to the stopcock.

Various modifications of the several embodiments disclosed will become apparent. This invention is intended to include such modifications to be limited only by the scope of the claims.

What is claimed is:

1. A universal, flexible container made of a polymeric material for the containment and delivery of medical fluids comprising:

a) first and second polymeric sheets having a square, round, oval, hexagonal, octagonal or rectangular configuration superimposed and sealed together at their periphery to form a pouch defining an interior, said pouch having a top portion and a bottom portion;

said bottom portion terminates in a first angle and a second angle of from about 5° to about 45° each from the center thereof and relative to a horizontal plane crossing the center of said bottom portion;

portions of said interior reservoir being mechanically or chemically embossed;

b) a combination access member of inverted Y shape configuration having:

b1) a stem with a proximal end and a distal end, said proximal end located at the bottom, center portion of the pouch sealed between said first and second polymeric sheets in the periphery thereof; and b2) a pair of tines having proximal and distal ends, the proximal ends thereof being integral with the stem of the access member;

the combination access member comprising:

1) an IV access frangible twist-off port at the distal end of the stem of the access member; and IV line having proximal and distal ends which is attached to the IV access frangible twist-off port at its proximal end, while at its distal end the IV line is equipped with a one-way luer slip stopcock, vent and a removable cap;

2) a needle access port located in one of the tines of the combination access member; and 3) a spike access port located in the other of the tines of the combination access member;

said needle and spike access ports being equipped with caps.

2. The universal, flexible container of claim 1 wherein the interior wall of said first sheet is embossed in a checkerboard fashion.

3. The universal flexible container of claim 2 wherein a 90° angle defined by said individual squares of said checkerboard points downward towards the access port of the container.

4. The universal, flexible container of claim 1 wherein the interior wall of said first sheet is embossed with micro circles or dots.

5. The universal, flexible container of claim 4 wherein said micro circles or dots have a diameter of at least 5 microns and are spaced from each other of form about 10 microns to about 10 millimeters.

6. The universal, flexible container of claim 1 wherein the interior wall of said first sheet is embossed with vertical channels in spaced relationship from each other oriented in a length-wise direction of the container.

7. The universal, flexible container of claim 6 wherein the width of each of said channels is of from about 0.01 to about 10 millimeters spaced from each other of from about 10 microns to about 10 millimeters.

8. The universal, flexible container of claim 1 wherein the interior wall of said first sheet is embossed with vertically oriented S-shaped channels in spaced relationship from each other oriented in a length-wise direction.

9. The universal, flexible container of claim 8 wherein the width of each of said S-shape channel is of from about 0.01 to about 10 millimeters spaced from each other of from about 10 microns to about 10 millimeters.

10. The universal, flexible container of claim 1 wherein said bottom portion terminates in a first and a second angle of from about 10° to about 30° each from the center thereof and relative to a horizontal plane crossing the center of said bottom portion.

11. The universal, flexible container of claim 1 wherein said bottom portion terminates in a first and a second angle of from about 10° to about 20° each from the center thereof and relative to a horizontal plane crossing the center of said bottom portion.

12. The universal, flexible container of claim 1 wherein said container further comprises at its top portion a heat welded periphery housing a hole therein for suspending said container during the filling process.

13. The universal, flexible container of claim 1 wherein said container further comprises at its bottom portion a heat welded periphery having a plurality of holes therein for suspending said container during delivery of content to the patient.

14. The universal, flexible container of claim 1, wherein said first and second polymeric sheets are made of polyvinylidene chloride sandwiched between two layers of polyethylene or polyvinylacetate.

15. The universal, flexible container of claim 1, wherein said first and second polymeric sheets are made of polyvinyl chloride.

16. The universal, flexible container of claim 1, wherein said first and second polymeric sheets are made of a polyethylene layer sandwiched between polyester outer layers sealed together by a propylene copolymer.

17. The universal, flexible container of claim 1, wherein said first and second polymeric sheets are made of polycyclohexanedimethylcyclohexane dicarboxylate.

18. The universal, flexible container of claim 1, wherein said first and second polymeric sheets are made of ethyl vinyl acetate.

19. A universal, flexible container made of a polymeric material for the containment and delivery of medical fluids comprising:

a) first and second polymeric sheets having a square, round, oval, hexagonal, octagonal or rectangular configuration superimposed and sealed together at their periphery to form a pouch defining an interior, said pouch having a top portion and a bottom portion;

said bottom portion terminates in a first angle and a second angle of from about 5° to about 45° each from the center thereof and relative to a horizontal plane crossing the center of said bottom portion;

portions of said interior reservoir being mechanically or chemically embossed;

b) a combination access member of inverted Y shape configuration having:

b1) a stem with a proximal end and a distal end, said proximal end located at the bottom, center portion of the pouch sealed between said first and second polymeric sheets in the periphery thereof; and b2) a pair of tines having proximal and distal ends, the proximal ends thereof being integral with the stem of the access member;

the combination access member comprising:

1) a one-way luer slip stopcock attached to the distal end of said stem;

a) an IV access frangible twist-off port attached to said one-way luer slip stopcock; and b) an IV line, having proximal and distal ends, attached to said IV access frangible twist-off port at the proximal end thereof, while at its distal end the IV line is equipped with a luer lock and cap;

2) a needle access port located in one of the tines of the combination access member; and 3) a spike access port located in the other of the tines of the combination access member;

said needle and spike access ports being equipped with caps.

20. The universal, flexible container of claim 19 wherein the interior wall of said first sheet is embossed in a checkerboard fashion.

21. The universal, flexible container of claim 20 wherein a 90° angle defined by said individual squares of said checkerboard points downward toward the access port of the container.

22. The universal, flexible container of claim 19 wherein the interior wall of said first sheet is embossed with micro circles or dots.

23. The universal, flexible container of claim 22 wherein said micro circles or dots have a diameter of at least 5 microns and are spaced from each other of from about 10 microns to about 10 millimeters.

24. The universal, flexible container of claim 19 wherein the interior wall of said first sheet is embossed with vertical channels in spaced relationship from each other oriented in a length-wise direction of the container.

25. The universal, flexible container of claim 24 wherein the width of each of said channels is of from about 0.01 to about 10 millimeters spaced from each other of from about 10 microns to about 10 millimeters.

26. The universal, flexible container of claim 19 wherein the interior wall of said first sheet is embossed with vertically oriented S-shape channels in spaced relationship from each other oriented in a length-wise direction.

27. The universal, flexible container of claim 26 wherein the width of each of said S-shape channel is of from about 0.01 to about 10 millimeters spaced from each other of from about 10 microns to about 10 millimeters.

28. The universal, flexible container of claim 19 wherein said bottom portion terminates in a first and a second angle of from about 10° to about 30° each from the center thereof and relative to a horizontal plane crossing the center of said bottom portion.

29. The universal, flexible container of claim 19 wherein said bottom portion terminates in a first and a second angle of from about 10° to about 20° each from the center thereof and relative to a horizontal plane crossing the center of said bottom portion.

30. The universal, flexible container of claim 19, wherein said container further comprises at its top portion a heat welded periphery housing a hole therein for suspending said container during the filling process.

31. The universal, flexible container of claim 19, wherein said first and second polymeric sheets are made of polyvinylidene chloride sandwiched between two layers of polyethylene or polyvinylacetate.

32. The universal, flexible container of claim 19, wherein said first and second polymeric sheets are made of polyvinyl chloride.

33. The universal, flexible container of claim 19, wherein said first and second polymeric sheets are made of a polyethylene layer sandwiched between polyester outer layers sealed together by a propylene copolymer.

34. The universal, flexible container of claim 19, wherein said first and second polymeric sheets are made of polycyclohexanedimethylcyclohexane dicarboxylate.

35. The universal, flexible container of claim 19, wherein said first and second polymeric sheets are made of ethyl vinyl acetate.

* * * * *